US008911781B2

(12) United States Patent
Antarkar et al.

(10) Patent No.: US 8,911,781 B2
(45) Date of Patent: Dec. 16, 2014

(54) PROCESS OF MANUFACTURE OF NOVEL DRUG DELIVERY SYSTEM: MULTILAYER TABLET COMPOSITION OF THIAZOLIDINEDIONE AND BIGUANIDES

(75) Inventors: Amit Krishna Antarkar, Nagpur (IN); Rajendra Ghanshamlal Lala, Mumbai (ID); Nirav Mahendra Kamdar, Mumbai (IN); Parag Narayan Gadkari, Thane (IN); Maya Janak Shah, Mumbai (IN); Janak Ramanlal Shah, Mumbai (IN)

(73) Assignee: Inventia Healthcare Private Limited, Mumbai (IN)

( * ) Notice: Subject to any disclaimer, the term of this patent is extended or adjusted under 35 U.S.C. 154(b) by 2603 days.

(21) Appl. No.: 10/518,044

(22) PCT Filed: Oct. 14, 2002

(86) PCT No.: PCT/IN02/00207
§ 371 (c)(1),
(2), (4) Date: Aug. 17, 2005

(87) PCT Pub. No.: WO03/105809
PCT Pub. Date: Dec. 24, 2003

(65) Prior Publication Data
US 2006/0057202 A1     Mar. 16, 2006

(30) Foreign Application Priority Data
Jun. 17, 2002 (IN) .......................... 533/MUM/2002

(51) Int. Cl.
| *A61K 9/48* | (2006.01) |
| *A61K 9/26* | (2006.01) |
| *A61K 9/24* | (2006.01) |
| *A61K 45/06* | (2006.01) |
| *A61K 9/20* | (2006.01) |
| *A61K 9/50* | (2006.01) |
| *A61K 31/155* | (2006.01) |
| *A61K 31/4439* | (2006.01) |

(52) U.S. Cl.
CPC .................. *A61K 9/209* (2013.01); *A61K 45/06* (2013.01); *A61K 9/2077* (2013.01); *A61K 9/5084* (2013.01); *A61K 31/155* (2013.01); *A61K 31/4439* (2013.01)
USPC ............ 424/472; 424/464; 424/468; 424/470

(58) Field of Classification Search
USPC ......... 424/424, 446, 448, 465, 469, 489, 490, 424/472
See application file for complete search history.

(56) References Cited

U.S. PATENT DOCUMENTS

| 4,351,825 A | 9/1982 | Sothmann et al. |
| 4,687,777 A | 8/1987 | Meguro et al. |
| 4,828,836 A | 5/1989 | Elger et al. |
| 4,834,985 A | 5/1989 | Elger et al. |
| 5,055,306 A | 10/1991 | Barry et al. |
| 5,100,669 A * | 3/1992 | Hyon et al. ................... 424/426 |
| 5,457,109 A | 10/1995 | Antonucci et al. |
| 5,478,852 A | 12/1995 | Olefsky et al. |
| 5,789,393 A | 8/1998 | Dressman et al. |
| 5,922,769 A | 7/1999 | Barelli et al. |
| 5,952,356 A | 9/1999 | Ikeda et al. |
| 5,955,106 A | 9/1999 | Moeckel et al. |
| 5,965,584 A | 10/1999 | Ikeda et al. |
| 6,011,049 A | 1/2000 | Whitcomb |
| 6,031,004 A | 2/2000 | Timmins et al. |
| 6,046,202 A | 4/2000 | Antonucci et al. |
| 6,046,222 A | 4/2000 | Antonucci et al. |
| 6,080,765 A | 6/2000 | Ikeda et al. |
| 6,099,859 A | 8/2000 | Cheng et al. |
| 6,099,862 A | 8/2000 | Chen et al. |
| 6,103,742 A | 8/2000 | Ikeda et al. |
| 6,117,451 A | 9/2000 | Kumar |
| 6,120,803 A | 9/2000 | Wong et al. |
| 6,121,294 A | 9/2000 | Ikeda et al. |
| 6,121,295 A | 9/2000 | Ikeda et al. |
| 6,133,293 A | 10/2000 | Ikeda et al. |
| 6,133,295 A | 10/2000 | Ikeda et al. |
| 6,150,383 A | 11/2000 | Ikeda et al. |

(Continued)

FOREIGN PATENT DOCUMENTS

| DE | 10016356 | 10/2001 |
| EP | 0 440 462 B1 * | 1/1991 |

(Continued)

*Primary Examiner* — Michael G Hartley
*Assistant Examiner* — Micah-Paul Young
(74) *Attorney, Agent, or Firm* — Blank Rome LLP

(57) ABSTRACT

A novel patient-convenient, cost effective pharmaceutical composition, comprising of thiazolidinediones and biguanide for controlling hyperglycemia manufactured as multilayer tablet and its process of manufacturing, for immediate release of thiazolidinediones or thiazolidinediones and biguanide and prolonged release of the biguanide only, the tablet comprising of minimum two layers wherein one outer layer comprises of a mixture of excipients and thiazolidinediones or thiazolidinediones and biguanide allowing immediate release of thiazolidinediones or thiazolidinediones and biguanide respectively and the other layer arranged in contact with the immediate release layer which comprises of a novel composition of excipients and a minimum one or more non-biodegradable, inert polymer(s) and the biguanide allowing pH independent prolonged release of the biguanide up to a period of 8-12 hours. The tablets are for once a day dosing. The tablets may optionally be film coated or enrobed by soft gelatin ribbons for additional protection against oxidation, photodegradation, identification, ease of swallowing, taste masking and for aesthetic appeal without altering the dissolution profile.

20 Claims, No Drawings

(56) References Cited

U.S. PATENT DOCUMENTS

| | | |
|---|---|---|
| 6,150,384 A | 11/2000 | Ikeda et al. |
| 6,156,773 A | 12/2000 | Ikeda et al. |
| 6,166,042 A | 12/2000 | Ikeda et al. |
| 6,166,043 A | 12/2000 | Ikeda et al. |
| 6,169,099 B1 | 1/2001 | Ikeda et al. |
| 6,169,100 B1 | 1/2001 | Ikeda et al. |
| 6,172,089 B1 | 1/2001 | Ikeda et al. |
| 6,172,090 B1 | 1/2001 | Ikeda et al. |
| 6,174,904 B1 | 1/2001 | Ikeda et al. |
| 6,211,205 B1 | 4/2001 | Ikeda et al. |
| 6,211,206 B1 | 4/2001 | Ikeda et al. |
| 6,211,207 B1 | 4/2001 | Ikeda et al. |
| 6,214,848 B1 | 4/2001 | Ikeda et al. |
| 6,218,409 B1 | 4/2001 | Ikeda et al. |
| 6,225,326 B1 | 5/2001 | Ikeda et al. |
| 6,232,330 B1 | 5/2001 | Ikeda et al. |
| 6,239,153 B1 | 5/2001 | Ikeda et al. |
| 6,251,924 B1 | 6/2001 | Ikeda et al. |
| 6,271,243 B1 | 8/2001 | Ikeda et al. |
| 6,274,605 B1 | 8/2001 | Ikeda et al. |
| 6,277,869 B1 | 8/2001 | Ikeda et al. |
| 6,284,275 B1 | 9/2001 | Chen et al. |
| 6,288,090 B1 | 9/2001 | Ikeda et al. |
| 6,296,874 B1 | 10/2001 | Cutie et al. |
| 6,303,146 B1 | 10/2001 | Bonhomme et al. |
| 6,303,640 B1 | 10/2001 | Ikeda et al. |
| 6,323,225 B1 | 11/2001 | Ikeda et al. |
| 6,329,403 B1 | 12/2001 | Odaka et al. |
| 6,329,404 B1 | 12/2001 | Ikeda et al. |
| 6,340,475 B2 | 1/2002 | Shell et al. |
| 6,368,626 B1 | 4/2002 | Bhatt et al. |
| 6,372,255 B1 | 4/2002 | Saslawski et al. |
| 6,372,790 B1 | 4/2002 | Bonhomme et al. |
| 6,384,062 B1 | 5/2002 | Ikeda et al. |
| 6,403,121 B1 | 6/2002 | Adjei et al. |
| 6,451,342 B2 | 9/2002 | Adjei et al. |
| 6,461,639 B2 | 10/2002 | Adjei et al. |
| 6,475,521 B1 * | 11/2002 | Timmins et al. .............. 424/469 |
| 6,491,950 B1 | 12/2002 | Gutierrez-Rocca et al. |
| 6,495,162 B2 | 12/2002 | Cheng et al. |
| 6,524,618 B1 | 2/2003 | Kumar et al. |
| 6,548,083 B1 | 4/2003 | Wong et al. |
| 6,586,438 B2 | 7/2003 | Piper |
| 6,660,300 B1 | 12/2003 | Timmins et al. |
| 6,667,054 B2 | 12/2003 | Sherman |
| 6,676,966 B1 | 1/2004 | Odidi et al. |
| 6,677,358 B1 | 1/2004 | Muller |
| 6,682,759 B2 | 1/2004 | Lim et al. |
| 6,693,094 B2 | 2/2004 | Pearson et al. |
| 6,723,340 B2 | 4/2004 | Gusler et al. |
| 6,734,197 B2 | 5/2004 | Randazzo et al. |
| 6,790,459 B1 | 9/2004 | Cheng et al. |
| 2001/0018070 A1 | 8/2001 | Shell et al. |
| 2001/0024659 A1 | 9/2001 | Chen et al. |
| 2001/0034374 A1 | 10/2001 | Adjei et al. |
| 2001/0036478 A1 | 11/2001 | Adjei et al. |
| 2001/0036479 A1 | 11/2001 | Cave et al. |
| 2001/0046515 A1 | 11/2001 | Adjei et al. |
| 2002/0002186 A1 | 1/2002 | Ikeda et al. |
| 2002/0004515 A1 | 1/2002 | Smith |
| 2002/0016287 A1 | 2/2002 | Buckingham et al. |
| 2002/0051820 A1 | 5/2002 | Shell et al. |
| 2002/0064556 A1 | 5/2002 | Cheng et al. |
| 2003/0091630 A1 * | 5/2003 | Louie-Helm et al. ......... 424/468 |
| 2003/0104059 A1 | 6/2003 | Chawla et al. |
| 2003/0139461 A1 | 7/2003 | Li et al. |
| 2003/0171407 A1 | 9/2003 | Freese et al. |
| 2003/0187074 A1 | 10/2003 | Hussain et al. |
| 2003/0219482 A1 | 11/2003 | Chaudhari et al. |
| 2003/0224046 A1 | 12/2003 | Rao et al. |
| 2003/0232078 A1 | 12/2003 | Dong et al. |
| 2004/0002544 A1 | 1/2004 | Makino et al. |
| 2004/0014797 A1 | 1/2004 | Moinet et al. |
| 2004/0022849 A1 | 2/2004 | Castan et al. |
| 2004/0034065 A1 | 2/2004 | Allison et al. |
| 2004/0039031 A1 | 2/2004 | Cugnardey et al. |
| 2004/0052848 A1 | 3/2004 | Cheng et al. |
| 2004/0059001 A1 | 3/2004 | Murpani et al. |
| 2004/0076667 A1 | 4/2004 | Kumar Gidwani et al. |
| 2004/0077730 A1 | 4/2004 | Bailey et al. |
| 2004/0081697 A1 | 4/2004 | Lewis et al. |
| 2004/0086562 A1 | 5/2004 | Shanghvi et al. |
| 2004/0086566 A1 | 5/2004 | Zhang |
| 2004/0096499 A1 | 5/2004 | Vaya et al. |
| 2005/0053661 A1 | 3/2005 | Tosetti et al. |

FOREIGN PATENT DOCUMENTS

| | | |
|---|---|---|
| EP | 0 440 462 A1 * | 8/1991 |
| EP | 1335708 | 8/2003 |
| WO | WO-9608243 | 3/1996 |
| WO | WO-9857634 | 12/1998 |
| WO | WO-9903477 | 1/1999 |
| WO | WO-9933448 | 7/1999 |
| WO | WO-9947128 | 9/1999 |
| WO | WO-0028989 | 5/2000 |
| WO | WO 0028989 A1 * | 5/2000 |
| WO | WO-0040233 | 7/2000 |
| WO | WO-0132157 | 5/2001 |
| WO | WO-0132158 | 5/2001 |
| WO | WO 0132158 A2 * | 5/2001 |
| WO | WO-0135940 | 5/2001 |
| WO | WO-0135941 | 5/2001 |
| WO | WO 0135941 A2 * | 5/2001 |
| WO | WO-0156544 | 8/2001 |
| WO | WO-0228181 | 4/2002 |
| WO | WO-0236100 | 5/2002 |
| WO | WO-02094285 | 11/2002 |
| WO | WO-03026637 | 4/2003 |
| WO | WO-03028704 | 4/2003 |
| WO | WO-03039527 | 5/2003 |
| WO | WO-03047529 | 6/2003 |
| WO | WO-03061643 | 7/2003 |
| WO | WO-2004082591 | 9/2004 |
| WO | WO-2005094794 | 10/2005 |
| WO | WO-2006107528 | 10/2006 |

* cited by examiner

PROCESS OF MANUFACTURE OF NOVEL DRUG DELIVERY SYSTEM: MULTILAYER TABLET COMPOSITION OF THIAZOLIDINEDIONE AND BIGUANIDES

BACKGROUND OF INVENTION

Diabetes mellitus is a major health care problem not only in the developing countries but also in the developed countries The main therapeutic goal in Type 2 Diabetes Mellitus (DM) ie non-insulin dependent Diabetes Mellitus is to control hyperglycemia which is due to derangement's of insulin resistance & impaired insulin secretion, altered lipemia, affected glucose metabolism and other factors & prevent hypoglycemia due to drug therapy.

It has now been proved that combination therapy with two or more antidiabetic agents belonging to different class often results in dramatic improvement in glycemic control, and a better control can be achieved through combination therapy compared to using a large dose of single active ingredient. A combination of antidiabetic agents results in additive or synergistic therapeutic effect, which can restore glucose control when one single agent alone is not successful. Accordingly, such combinations are useful in treating diabetes and associated complications.

Thiazolidinediones such as Pioglitazone HCl is a new class of compounds and are insulin sensitivity enhancers. The plasma elimination half-life (t½) for Pioglitazone HCl at steady state concentrations is 3.3-4.9 hours. The metabolites of Pioglitazone HCl are active in-vivo. Hence, for total Pioglitazone HCl (parent drug and metabolites) the t½ is 16 to 24 hours [Gillies P S & Dunn C J. Drugs 2000; 60(2): 333-343].

Biguanide, in particular Metformin HCl, increases the sensitivity to insulin in peripheral tissues of the hosts. Metformin HCl is also involved in inhibition of glucose absorption from the intestine, suppression of hepatic gluconeogenesis, and inhibition of fatty acid oxidation. It has an absolute oral bioavailability of 40 to 60% and gastro-intestinal absorption is apparently complete within 6 hours of the ingestion. An inverse relation is observed between the dose ingested and the relative absorption with the therapeutic doses of ranging from 0.5 to 1.5 gm, suggesting the involvement of active, saturable absorption process.

The plasma half-life of Metformin HCl is 1.5-4.9 hours [Bailey C J et al. New Eng. Journal of Medicine 1996; 334: 574-579]. Suitable dosage regimens of Metformin HCl include unit doses of 500 mg two to three time's daily and can even be build upto five times daily or 850 mg once or twice daily. [Martindale, The Complete Drug Reference. Sweetman S. C. (Ed) 33rd Ed 2002]

Metformin HCl and Pioglitazone HCl have differing mode of peripheral action, which leads to synergy of drug action and better control of diabetic state. Multiple dosing regimens together, along with large doses, dose dependent absorption, poor bioavailability of Metformin HCl are not preferred since it leads to patient non-compliance, potential side effects & danger of overdosing. It is therefore imperative to shift from multiple dosing to once-a-day or twice-a-day dosing regimens. Longer plasma elimination half-life of Pioglitazone HCl substantiates the recommendation of once daily dosing regimen of Pioglitazone HCl.

The need has therefore been to provide formulations and processes to deliver the active pharmaceutical ingredients ensuring prolonged release of Metformin HCl and instant release Pioglitazone HCl from the formulation when consumed.

PRIOR ART

U.S. Pat. Nos. 6,011,049, 6,150,384, 5,965,584, and 5,952,356 recommended separate or co-administration of Metformin HCl and Pioglitazone HCl. However they do not teach the art of formulation or preparing a single integral unit containing a combination of the drugs or single integral unit where biguanide has prolonged release characteristics.

U.S. Pat. Nos. 6,296,874, 6,403,121, US Patent Applications 20010036478, 20010034374, 20010046515 describe core formulation of either Troglitazone or Pioglitazone HCl microspheres covering Metformin HCl microspheres core to provide single integral unit. The treatment done not require the prolonged release of Pioglitazone HCl or Troglitazone, as the drug inherently has longer half-life. The patents also recommend the tailoring the formulations as per the patient's need, which is difficult to manufacture on a mass scale. Moreover the manufacture of such formulations involves a number of cumbersome steps making it unattractive for industrial operations.

PCT Publication WO 01/35940, describes the use of Thiazolidinedione derivatives especially one described in EP0306228 along with another anti-diabetic agent Metformin HCl as a single integral unit multilayer tablet. The thiazolidinedione is formulated on the surface of Metformin HCl tablet using a coating technique. The release of both the drugs is immediate. This art does not teach how to formulate prolonged release of Metformin HCl and immediate release of Pioglitazone HCl in a single dosage form.

PCT Publication WO01/35941 describes the use of Thiazolidinedione derivatives especially one described in EP0306228 along with another anti-diabetic agent Metformin HCl as a single integral unit tablet or multilayer tablet. The thiazolidinedione and suitable carrier are formulated with Metformin HCl and its carrier in a single tablet or they are compressed into multi layer tablet with intention to solve incompatibility observed between Polyvinyl pyrollidone and Thiazolidinedione. This formulation and dosage form has a major shortcoming as the formulation and the tablet form demonstrates the simultaneous release of both the drugs. This is not a desirable feature.

PCT Publication No. WO 00/28989 describes the use of Thiazolidinedione derivatives described in EP0306228 along with another anti-diabetic agent such as Metformin HCl as a single integral unit single layer or multilayer tablet. It claims to sustain or delay the release of thiazolidinedione alone or both the drugs. Sustained release or delayed release of thiazolidinedione is not desired due to the inherent long half-life of the drug. The publication does not teach the art of selectively prolonging the release of Metformin HCl with immediate release of Thiazolidinedione.

U.S. Pat. No. 5,955,106 describes a process for the preparation of Metformin HCl 850 mg retard tablet, containing hydrocolloid forming retarding agent and further coating it to have a retarding film envelope for controlling the release of drug. The process involves tabletting of the Metformin core, to marginally retard its release with the major retardation in release resulting from the retarding film coat. The patent does not in any manner teach the manufacture of bi-layered compositions containing Metformin HCl and Pioglitazone HCl where it is desirable to prolong the release of Metformin HCl.

PCT Publication No. WO 9947128 describes the preparation of Metformin HCl controlled release tablet using biphasic delivery where Metformin HCl is blended with a hydrophilic or hydrophobic polymer to form granules, which are further dispersed or embedded in one or more hydrophilic or hydrophobic polymer or material. However if these biphasic granules are to be used for the preparation of bilayered tablets of Metformin HCl and sulfonyl urea or thiazolidinedione, the size of the tablet becomes relatively large causing inconvenience in swallowing.

Marketed antidiabetic combination preparation is Glucovance RTM, of Bristol Myers Squibb (Physician Desk Reference, Ed.55, Pg. 3477), which comprises of Metformin HCl and Glyburide as a single integral unit immediate release tablet.

Thus there is no prior art that teaches patient-convenient cost effective pharmaceutical compositions and the manufacture of granules containing biguanide capable of being compressed into tablets with pH independent prolonged release of the biguanide. Further the prior art does not teach compositions and manufacture of granules containing biguanide capable of being compressed into bilayered tablets with the other layer comprising of active pharmaceutical ingredients belonging to class of thiazolidinedione, sulfonyl ureas, alpha-glucosidase inhibitor, aldose reductase inhibitor, statins compound, squalene synthesis inhibitor, fibrates, angiotensin converting enzymes inhibitor, LDL catabolism enhancers for desired layer-selective immediate release of these active pharmaceutical ingredients and pH independent, prolonged in-vitro release of biguanide. The prior art also does not teach compositions and methods of manufacturing of multiplayer tablets with such characteristics.

OBJECTS OF THE INVENTION

The object of the invention is to provide process for the manufacture of patient convenient, cost effective antihyperglycemic pharmaceutical compositions in multi-layered tablet dosage form capable of layer-selective prolonged release of one active pharmaceutical ingredient(s) in the group of biguanides and layer-selective of immediate release of another active pharmaceutical ingredients belonging to the group of thiazolidinediones, sulfonyl ureas, alpha-glucosidase inhibitor, aldose reductase inhibitor, statins compound, squalene synthesis inhibitor, fibrates, angiotensin converting enzymes inhibitor, LDL catabolism enhancers.

Another object of the invention is to provide process for the manufacture of patient convenient, cost effective antihyperglycemic pharmaceutical compositions in bilayered tablet dosage form capable of layer-selective prolonged release of one active pharmaceutical ingredient(s) in the group of biguanides and layer-selective of immediate release of active pharmaceutical ingredient(s) belonging to the group of thiazolidinediones.

It is another object of the invention to provide novel composition of granules containing biguanides that are capable of being effectively compressed into a single tablet system exhibiting pH independent prolonged release of biguanide.

It is yet another object of the invention to provide novel composition of granules containing biguanides that are capable of being effectively compressed into a multilayered tablet system for desired layer-selective prolonged and immediate release of the active pharmaceutical ingredients.

It is further an object of the invention to provide prolonged release granules containing Metformin HCl which are suitable for preparation of multi-layered/bi-layered tablets with layer selective drug release characteristics that are stable on prolonged storage without altering the granule characteristics such as moisture content, flowability etc. and compression characteristic such as hardness, friability etc.

It is another object to provide a process for manufacturing pharmaceutical composition in a multi layered tablet form capable of layer-selective prolonged release of Metformin HCl and layer-selective immediate release of Pioglitazone HCl.

It is yet another object of the invention to provide process for the manufacture of bi-layered tablet of the antihyperglycemic pharmaceutical composition, wherein the layer containing Metformin HCl exhibits prolonged release and the layer containing Pioglitazone HCl exhibits immediate release profiles.

It is yet another object of the invention to provide process for the manufacture of a multi-layered/bi-layered tablet wherein the layer-selective drug release profiles are predictable and exhibit reproducible in-vivo performance without the problems of dose dumping and burst effect of the formulation.

It is further an object of the invention to provide process for the manufacture of multi-layered tablets described herein, where the prolonged release of Metformin HCl layer is pH independent and the formulation processed for once a day dosing.

It is further an object of the invention to release Pioglitazone HCl immediately from layers of the multi-layer tablet and made available for the absorption.

It is further an object of the invention to provide the above-mentioned multi-layered tablets of desired hardness, low friability without capping.

It is further an object of the invention to provide novel composition for the manufacture of "once a day" multi-layered tablets wherein the release of Metformin HCl is pH independent and prolonged whereas the release of Pioglitazone HCl is immediate such that the size of the tablet is convenient to swallow.

It is further an object of the invention to provide a formulation and dosage form to ensure bioavailability and minimal inter-patient variation in the pharmacokinetic parameters.

SUMMARY OF THE INVENTION

Novel compositions of the present invention is processed to prepare granules for the manufacture of patient convenient, cost effective pharmaceutical compositions in multi-layered tablet dosage form capable of layer-selective prolonged release of one active pharmaceutical ingredient(s) in the group of biguanides and layer-selective of immediate release of active pharmaceutical ingredient(s) belonging to the group of thiazolidinediones, sulfonyl ureas, alpha-glucosidase inhibitor, aldose reductase inhibitor, statins compound, squalene synthesis inhibitor, fibrates, angiotensin converting enzymes inhibitor, LDL catabolism enhancers.

Also novel compositions of the present invention is processed to prepare a multilayered tablet for example in the limiting case of a bilayered tablet with minimum two superimposed layers, characterized in that A layer containing novel composition of the active pharmaceutical ingredient(s) or their pharmaceutically acceptable salts belonging to the class Thiazolidinedione e.g.

Pioglitazone HCl with or without Biguanide e.g Metformin HCl and a mixture of desired excipients and Another layer, containing novel composition of the drugs or its pharmaceutically acceptable salt belonging to the class of Biguanide e.g. Metformin HCl, one or more polymers and desired excipients which is in contact with the first layer, are manufactured using specially formulated and processed granules containing Metformin HCl capable of being compressed into a layer to allow the pH independent, in-vitro prolonged release of Metformin HCl up to a period of 8-12 hours from selective layer and processed granules containing thiazolidinedione e.g. Pioglitazone HCl for immediate release of thiazolidinediones from the other selective layer.

The bi-layered tablet features may be extended to provide process for the manufacture of antihyperglycemic pharmaceutical compositions in multi-layered tablet dosage form capable of layer-selective prolonged release of active pharmaceutical ingredient(s) in the group of biguanides and layer-selective immediate release active pharmaceutical ingredient(s) belonging to the group of thiazolidinediones.

The manufacturing process involves the separate preparation of specially formulated granules containing Metformin HCl and Pioglitazone HCl and then compressing them into multilayered tablets exhibiting prolonged pH independent in-vitro release of Metformin HCl upto a period of 8-12 hours and immediate release of Pioglitazone HCl.

The tablets so prepared show hardness of 6.0-12.0 Kgs/sq.cm, minimal friability and no capping.

The bilayered tablets may further be film coated for aesthetic appeal or enrobed into soft gelatin ribbons for ease of swallowing, additional protection against oxidation, photo-degradation, identification, taste masking, and or for aesthetic appeal without altering the dissolution profile.

The invention provides a fixed dose pharmaceutical composition suitable for management of diabetes mellitus, especially Type 2 diabetes mellitus and conditions associated with Type 2 diabetes mellitus

DETAILED DESCRIPTION OF THE INVENTION

Thus in accordance with this invention, in the limiting case of a multi-layered tablet as a bilayered tablet offers options where;
  a) Both the layers are parallel to each other i.e. the second layer has upper surface & lower surface, only one of those surfaces being in contact with the first layer the shape of the tablet being generally capsule shaped or of any shape provided the release profile of the drug is not changed.
  b) The second layer is either completely covered by the first layer or only partially covered by it.

The active pharmaceutical ingredient(s) of the composition can be selected from the group belonging to the class of Biguanide, thiazolidinediones, sulfonyl ureas, alpha-glucosidase inhibitor, aldose reductase inhibitor, statins compound, squalene synthesis inhibitor, fibrates, angiotensin converting enzymes inhibitor, LDL catabolism enhancers and their pharmaceutically acceptable salts.

For the purposes of describing the invention active pharmaceutical ingredient(s) of the composition is selected from the group belonging to the class of Biguanide and Thiazolidinedione. Examples of the active pharmaceutical ingredients in the class of Biguanides include Phenformin, Buformin and Metformin and their pharmaceutically acceptable salts. Examples of active pharmaceutical ingredients in the class of Thiazolidinediones include Rosiglitazone, Troglitazone and Pioglitazone and their pharmaceutically acceptable salts.

For the purposes of describing the invention, Pioglitazone HCl and Metformin HCl are selected as the drug for the first layer (immediate release) and the second layer (prolonged release) respectively.

Alternatively, a part of Metformin HCl can also be added in the formulation of the immediate release layer, which is not more than 10% of the dose of Metformin HCl per tablet.

The dose of Metformin HCl per tablet is in the range of 250 mg-2000 mg and the dose of Pioglitazone HCl equivalent to Pioglitazone per tablet is in the range of 15-60 mg. and dosage regime is 1-4 tablets once a day.

The preferred strength for Metformin HCl per tablet in the bilayer formulation is 500 mg and Pioglitazone per tablet is either 15 mg or 30 mg. This invention is not limited to above mention fixed dose combination but will include other fixed dose combinations also.

Thus in accordance with one of the embodiments of this invention where both the layers are parallel to each other i.e. the second layer has upper surface & lower surface, only one of those surface being in contact with the first layer, the process comprises
  Formulation of the composition of the various layers that will finally be used to form the tablet.
  Preparing the specially formulated granules containing the drugs to be "prolonged released" or "immediate released" from the selective layers of the multi-layered tablet. The granulation may be done by the methods of "dry granulation" or "direct compression" or "wet granulation".
  Screening and sizing the prepared granules.
  Treating the screened and sized granules with lubricants.
  Appropriately compressing the granules to create the tablets having selective layers as desired.
  A] Granules containing Biguanides such as Metformin HCl of invention are prepared in following manner:
    1. Metformin HCl is pulverized to particle size of less than 100 microns or less.
    2. Metformin HCl is then blended with non-biodegradable, inert polymer(s). Blending is carried out in mixers such as planetary mixers, octagonal blenders, V-blenders or rapid mixer granulators or fluid bed granulators.
    3. This drug polymer(s) blend is then wet granulated using a solvent that may optionally contain polymer(s), binders and plasticizers. The granulation solvent may be water or hydroalcoholic solution. Granulation can be carried in granulator such rapid mixer granulator, fluid bed granulator, planetary mixer or any other mixer used for granulation.
    4. The granulated mass is dried and then sized using comminuting mill such as Fitz mill or oscillating granulator or any other equipment suitable for purpose, with an appropriate mesh preferably around 1-mm mesh.
    5. The granules are then mixed with Talc, magnesium stearate and colloidal silicon dioxide.
    6. The resultant lubricated granules containing Metformin HCl are ready for compression to form the selective prolonged release layer.
  B] Granules containing Thiazolidinedione salts such as Pioglitazone HCl are prepared by methods such as wet granulation or blended to prepare directly compressible blend or using dry granulation as follows:
    1. Pioglitazone HCl used is of particle size less than 30 microns.
    2. Blending of Pioglitazone HCl with fillers, disintegrants, binders, lubricants and permitted colours carried out in planetary mixer, octagonal blender, double cone blender, rotary mixer granulator, drum mixer, ribbon blender, fluid bed processor or any other suitable mixer.
    3. The resultant lubricated granules of Pioglitazone HCl are ready for compression to form a layer releasing the drug immediately from the bi-layered tablet or a set of layers of the multi-layered tablet.

Other active pharmaceutical ingredients belonging to the class of sulfonyl ureas, alpha-glucosidase inhibitor, aldose reductase inhibitor, statins compound, squalene synthesis inhibitor, fibrates, angiotensin converting enzymes inhibitor, LDL catabolism enhancers can also be granulated using method for preparation of granules containing Thiazolidinedione, which are ready for compression to form a layer releasing the active pharmaceutical ingredient(s) immediately from the bi-layered tablet or a set of layers of the multi-layered tablet.

C] The granules containing Biguanide and Thiazolidinedione are loaded in different hoppers of a tablet compression machine and then compressed into capsule shaped, biconvex, multilayered tablets having an immediate release of Thiazolidinedione (Pioglitazone HCl) and in-vitro pH independent prolonged release of Biguanide (Metformin HCl) upto a period of about 8 to about 12 hours. The shape of tablet is not limited to capsule shape and can vary so long as the desired drug release profile remains unaffected.

In another embodiments of invention formulation containing active pharmaceutical ingredient(s) such as sulfonyl urea, alpha-glucosidase inhibitor, aldose reductase inhibitor, statins compound, squalene synthesis inhibitor, fibrates, angiotensin converting enzymes inhibitor, LDL catabolism enhancers may be used instead of Thiazolidinedione as per therapeutic dose.

The fillers are selected but not limited to Microcrystalline Cellulose, Lactose, Dibasic Calcium Phosphate. The disintegrants are selected but not limited to sodium starch glycollate, crosscarmellose sodium, crosspovidone, starch, pregelatinized starch, low substituted Hydroxypropylcellulose. The binders are selected but not limited to Hydroxypropylmethylcellulose, Polyvinylpyrrolidone, and Hydroxypropylcellulose. The lubricating agents or glidants or antiadherants are selected but not limited to talc, Colloidal silicon dioxide, stearic acid, magnesium stearates, and calcium stearates.

The invention is not limited to carrying out a wet granulation method for the formulation that finally forms a set of the layers (e.g. the second layer in a bi-layered tablet) and direct compression method for the formulation that finally forms the other set of layers (e.g. the first layer in a bi-layered tablet). The formulations in the present invention may alternatively be processed by a range of granulation techniques to prepare the granules for use in the preparation of the various layers in the tablet.

The layer from which the release of Metformin HCl is prolonged comprises of one or more inert, non-biodegradable polymer(s), which swells & erodes in aqueous media & subsequently, releases the drug in the surrounding environment. The polymer is selected but not limited to Hydroxypropylmethylcellulose alone or combination of Hydroxypropylmethylcellulose with Sodium Carboxymethylcellulose or combination of Hydroxypropylmethylcellulose with Hydroxypropylcellulose or combination of Hydroxypropylmethylcellulose with Hydroxyethylcellulose or combination of Hydroxypropylmethylcellulose with Sodium Alginate or combination of Hydroxypropylmethylcellulose with Xanthan Gum or combination of Hydroxypropylmethylcellulose with Guar gum or combination of Hydroxypropylmethylcellulose with Sodium Carboxymethylcellulose and Meth (acrylic) acid Copolymers or combination of Hydroxypropylmethylcellulose with Sodium Alginate and Meth(acrylic) acid copolymer.

The copolymers derived from (meth) acrylic acids comprise the copolymers of derivatives of methacrylic acid and the copolymers of derivatives of acrylic acid and of derivatives of methacrylic acid. According to a preferred embodiment of the invention, the non-biodegradable inert polymeric material is chosen from the groups consisting of ethyl acrylate and methyl methacrylate copolymers, ethylammonium methacrylate and methyl acrylate copolymers, ethylammonium methacrylate and ethyl acrylate copolymers, ethylammonium methacrylate and methyl methacrylate copolymers, ethylammonium methacrylate and ethyl methacrylate copolymers, methacrylic acid and ethyl acrylate copolymers, methacrylic acid and methyl methacrylate copolymers. Among these polymers copolymers of methacrylic acid and ethyl acrylate the preferred molecular weight are >100,000 daltons.

The nominal viscosity at 20° C. of a 2% w/w aqueous solution of Hydroxypropylmethylcellulose used is not less than 300 cP. The nominal viscosity of a 1% w/w aqueous solution of Sodium alginate at 20° C. is not less than 50 cP. The nominal viscosity of a 1% w/w aqueous dispersion of Guar gum is not less than 2000 cP.

The nominal viscosity at 25° C. of a 1% w/w aqueous solution of

Hydroxypropylcellulose is not less than 1500 cP.
Hydroxyethylcellulose is not less than 1500 cP.
Sodium Carboxymethylcellulose is not less than 1500 cP.
Xanthan gum is not less than 1200 cP The formulation for the layer containing the Biguanide say Metformin HCl contains at least 35% of a polymer or a combination of the polymers and preferably between 40-65% by weight of the Biguanide say Metformin HCl. The polymer combinations may vary as follows: in case of combination of two polymers, the polymers are used in the ratio of 1:0.01-1:3.5 and in case of combination of three polymers, the polymers are used in the ratio of 1:0.01:0.1-1:3.5:0.5 depending on the polymers used.

The addition sequence of the polymer(s) is designed to achieve the desired final characteristics of the end product.

In the case of a bi-layered tablet, prolonged release layer comprises of drug Metformin HCl which is about 50% to about 80% by weight of the layer and immediate release layer comprises drug Pioglitazone HCl in the range of 5-50% of this layer.

The respective weight ratio of first layer and the second layer are not critical to the process of the invention and are adjusted according to the desired dosage.

The bilayered tablet which is formulated may be further enrobed into soft gelatin ribbons for ease of swallowing &/or for additional protection against photodegradation & oxidation &/or for taste masking and/or identification and/or for aesthetic appeal without altering the dissolution profile.

EXAMPLES

The invention is now illustrated with non-limiting examples for the preparation of bilayered tablets.

Example 1

The formulation for the preparation of the Metformin HCl prolonged release layer is as follows:

| | |
|---|---|
| Metformin HCl | 60.0% |
| Hydroxypropylmethylcellulose K4M | 37.0% |
| Polyvinylpyrrolidone K30 | 0.75% |
| Talc | 0.50% |
| Colloidal Silicon Dioxide | 1.50% |
| Magnesium stearate | 0.25% |
| Isopropyl Alcohol | qs |
| Purified Water | qs |

Pulverized Metformin HCl and Hydroxypropylmethylcellulose are introduced in a mixer granulator and mixing is carried out for 10 minutes. Polyvinylpyrrolidone K30 is dissolved in granulating solvent (Isopropyl alcohol and water in the ratio of 80:20). This solution is then added or sprayed on to the resultant mixture into the mixer granulator to form granules. The granules are then dried in hot air oven or fluid bed drier to moisture content between 0.5-3.5%. The dried granules are then sized using multi-mill to a desired size (1.5 mm or less) and the sized granules are lubricated with Talc, Colloidal Silicon Dioxide and Magnesium stearate and the resultant lubricated granules containing Metformin HCl are ready for compression to form a prolonged release layer.

The formulation for the preparation of selective layer showing immediate release is as follows:

| Pioglitazone HCl | 20.05% w/w |
| Microcrystalline Cellulose | 24% w/w |
| Sodium Starch glycollate | 10% w/w |
| L-HPC(LH 21) | 9.0% w/w |
| Lactose | 28.6 w/w |
| Hydroxypropylmethylcellulose | 1.2% w/w |
| Talc | 1.8% w/w |
| Colloidal Silicon Dioxide | 3.65% w/w |
| Magnesium stearate | 0.5% w/w |
| Approved Lake colorant | 1.2% w/w |

Pioglitazone HCl is blended with microcrystalline cellulose, Sodium starch glycollate, L-hydroxypropylcellulose (L-HPC [LH-21]), lactose and hydroxypropylmethylcellulose in a suitable mixer. Mixing is carried out for 10 minutes. Optionally the blend may be compacted and sized. Colorant, colloidal silicon dioxide, talc and magnesium stearate is then introduced in the mixer and mixing is carried for 10 minutes. The resultant lubricated granules containing Pioglitazone HCl are ready for compression to form a first layer.

The said granules containing Metformin HCl and Pioglitazone HCl are loaded in two different hopper of a tablet compression machine and then compressed into capsule shaped, biconvex, bilayered tablets.

Example 2

Another example for the preparation of the Metformin HCl Prolonged release layer is as follows

| Metformin HCl | 60.0% w/w |
| Hydroxypropylmethylcellulose | 29% w/w |
| Xanthan Gum | 9.25 w/w |
| Polyvinylpyrrolidone k30 | 0.25 w/w |
| Talc | 0.5 w/w |
| Colloidal Silicon Dioxide | 0.75 w/w |
| Magnesium stearate | 0.25 w/w |
| Isopropyl Alcohol | qs |
| Purified Water | qs |

Example 3

Another example for the preparation of the Metformin HCl Prolonged release layer is as follows

| Metformin HCl | 60.0% w/w |
| Hydroxypropylmethylcellulose | 9.0% w/w |
| Sodium Carboxymethylcellulose | 25.4% w/w |
| Methacrylic acid copolymer dispersion | 3.5% w/w |
| Polyethylene Glycol 6000 | 0.35% w/w |
| Polyvinylpyrrolidone k30 | 0.25% w/w |
| Talc | 0.5% w/w |
| Colloidal Silicon Dioxide | 0.75% w/w |
| Magnesium stearate | 0.25% w/w |
| Purified water | qs |

Metformin HCl, Hydroxypropylmethylcellulose, Sodium carboxymethylcellulose are mixed and further granulated with methacrylic acid copolymer dispersion containing binder and plasticizer.

Alternatively, granules containing Pioglitazone HCl as a selective immediate release layer can also be prepared by wet granulation method, the example for which is given below.

| Pioglitazone HCl | 20.05% w/w |
| Microcrystalline Cellulose | 30.3% w/w |
| Sodium Starch glycollate | 10% w/w |
| Lactose | 34.5 w/w |
| Hydroxypropylmethylcellulose | 1.2% w/w |
| Talc | 1.0% w/w |
| Colloidal Silicon Dioxide | 1.25% w/w |
| Magnesium stearate | 0.5% w/w |
| Approved Lake colorant | 1.2% w/w |
| Purified water | qs |

Pioglitazone HCl is blended with microcrystalline cellulose, Sodium Starch glycollate and Lactose in a suitable mixer granulator. Mixing is carried out for 10 minutes.

The mix is then granulated with hydroxypropylmethylcellulose solution in water. The granules are then dried to moisture content between 0.5-2.50%.

In other embodiments of invention formulation containing active pharmaceutical ingredient(s) such as sulfonyl urea, alpha-glucosidase inhibitor, aldose reductase inhibitor, statins compound, squalene synthesis inhibitor, fibrates, angiotensin converting enzymes inhibitor, LDL catabolism enhancers may be used instead of Thiazolidinedione as per therapeutic dose.

The dried granules are then sized using multimill to a desired size (1.5 mm or less) and the sized granules are lubricated with colorant, talc, colloidal silicon dioxide and magnesium stearate and the resultant lubricated granules containing Pioglitazone HCl are ready for compression.

Dissolution and In-Vitro Drug Release Profile

The tablets are analyzed using USP Dissolution Apparatus II. The Dissolution Media for Metformin HCl is either Distilled Water or 0.1 N HCl or pH 6.8 Phosphate Buffer, Media Volume 900 ml. The release specification is given below.

| Time Interval (Hours) | Range of % Drug Released |
|---|---|
| 1 | 25-45 |
| 4 | 50-80 |
| 8 | Not less than 75% |

The Dissolution Media for Pioglitazone HCl is 0.1N HCl, Media Volume 900 ml and its release specification is given below.

| Time Interval (min) | Range of % Drug Released |
|---|---|
| 30 | Not less than 80 |

The in-vitro dissolution profile achieved with bilayer tablet formulation of above described example in 0.1N HCl or 6.8 pH Phosphate buffer or Distilled water for Metformin HCl using dissolution apparatus USP Type II with 900 ml media volume is as follows.

| Time Interval (Hours) | Cumulative % Drug Released |
|---|---|
| 1 | 28-38 |
| 4 | 65-72 |
| 8 | 85-95 |

The in-vitro dissolution profile achieved with bilayer tablet formulation of above described example in 0.1N HCl Pioglitazone HCl using dissolution apparatus USP Type II with 900 ml media volume is as follows.

| Time Interval (minutes) | % Drug Released |
|---|---|
| 10 | >85% |

We claim:

1. A process for the manufacture of a bi-layered tablet dosage form for once a day administration, the process comprising:
   a) preparing a first granule formulation comprising at least one non-biodegradable inert polymer and a biguanide, or a pharmaceutically acceptable salt thereof, of particle size less than 100 microns to achieve pH independent prolonged in-vitro release of the biguanide or pharmaceutical acceptable salt thereof, wherein the non-biodegradable inert polymer is present in an amount of at least 35% by weight of biguanide in the dosage form;
   b) preparing a second granule formulation comprising (i) one or more active pharmaceutical ingredients for immediate release selected from thiazolidinediones, sulfonyl ureas, alpha-glucosidase inhibitors, aldose reductase inhibitor inhibitors, statins, squalene synthesis inhibitors, fibrates, angiotensin converting enzymes inhibitor, LDL catabolism enhancers, and pharmaceutically acceptable salts thereof; and (ii) a non-biodegradable inert polymer;
   c) treating the first and second granule formulations with lubricants; and
   d) compressing the first and second granule formulations to form the bilayered tablet dosage form;
   wherein the content of non-biodegradable inert polymer in the second granule formulation is not more than 1.2% by weight of the lubricated second granule formulation, the tablet dosage form contains layers of the first and second granule formulations, and the tablet dosage form provides monophasic prolonged release of the biguanide.

2. The process of claim 1, wherein the biguanide is Metformin, Buformin, Phenformin, or a pharmaceutical acceptable salt thereof, and the thiazolidinedione is Pioglitazone, Rosiglitazone, Troglitazone, or a pharmaceutically acceptable salt thereof, or a mixture thereof.

3. A process as claimed in claim 1, wherein the non-biodegradable inert polymer is selected from cellulose derivatives, (meth) acrylic acid co-polymers, xanthan gum, guar gum, alginates and pharmaceutical acceptable salt thereof and mixtures thereof.

4. A bi-layered pharmaceutical dosage form for once a day administration comprising,
   a) a first layer comprising granules of at least one non-biodegradable inert polymer and a biguanide, or a pharmaceutically acceptable salt thereof, of particle size less than 100 microns for pH independent prolonged in-vitro release of the biguanide or a pharmaceutical acceptable salt thereof, wherein the non-biodegradable inert polymer is present in an amount of at least 35% by weight of biguanide in the dosage form; and
   b) a second layer for immediate release comprising (i) one or more active pharmaceutical ingredients, or pharmaceutical acceptable salts thereof, selected from thiazolidinediones, sulfonyl ureas, alpha-glucosidase inhibitors, aldose reductase inhibitors, statins squalene synthesis inhibitors, fibrates, angiotensin converting enzymes inhibitors, and LDL catabolism enhancers and (ii) a non-biodegradable inert polymer;
   wherein the content of non-biodegradable inert polymer in the second layer is not more than 1.2% by weight of the second layer, and the dosage form provides monophasic prolonged release of the biguanide.

5. A composition as claimed in claim 4, wherein the biguanide is Metformin, Buformin, Phenformin, or a pharmaceutical acceptable salt thereof, and the thiazolidinedione is Pioglitazone, Rosiglitazone, Troglitazone, or a pharmaceutically acceptable salt thereof, or a mixture thereof.

6. A composition as claimed in claim 4, wherein the non-biodegradable inert polymer is selected from cellulose derivatives, (meth)acrylic acid co-polymers, xanthan gum, guar gum, alginates and pharmaceutical acceptable salts thereof and mixtures thereof.

7. A composition as claimed in claim 4, wherein the second layer comprises Pioglitazone hydrochloride of particle size less than 30 microns, and at least one excipient selected from fillers, disintegrants and binders.

8. A composition as claimed in claim 6, wherein the cellulose derivatives are selected from alkylcellulose, hydroxyalkylcellulose, carboxyalkylcellulose preferably methylcellulose, ethylcellulose, hydroxyethylcellulose, hydroxypropylmethylcellulose, methylhydroxyethylcellulose, hydroxymethylcellulose, hydroxypropylcellulose, carboxymethylcellulose, sodium carboxymethylcellulose and calcium carboxymethylcellulose, and combinations thereof.

9. A composition as claimed in claim 4, wherein the non-biodegradable inert polymer is selected from (i) a mixture of hydroxypropylmethylcellulose and hydroxypropylcellulose; (ii) a mixture of hydroxypropylmethylcellulose and hydroxyethylcellulose; (iii) a mixture of hydroxypropylmethylcellulose and sodium carboxymethylcellulose; (iv) a mixture of hydroxypropylmethylcellulose and sodium alginate; (v) a mixture of hydroxypropylmethylcellulose and Xanthan gum; and (vi) a mixture of hydroxypropylmethylcellulose and guar gum; in a ratio ranging from 1:0.01 to 1:3.5, and the non-biodegradable inert polymer is present in an amount of at least 35% by weight of the biguanide.

10. A composition as claimed in claim 4, wherein the non-biodegradable inert polymer is selected from (i) a mixture of hydroxypropylmethylcellulose, sodium carboxymethylcellulose and methacrylic acid copolymer, and (ii) hydroxypropylmethylcellulose, sodium alginate and methacrylic acid copolymer, at a ratio of 1:0.01:0.1 to 1:3.5:0.5 respectively, and the non-biodegradable inert polymer is present in an amount of at least 35% by weight of the biguanide.

11. A composition as claimed in claim 6, wherein the nominal viscosity at 20° C. of a 2% w/w aqueous solution of hydroxypropylmethylcellulose used is not less than 3000 cP, the nominal viscosity of a 1% w/w aqueous solution of sodium alginate at 20° C. is not less than 50 cP and the nominal viscosity of a 1% w/w aqueous dispersion of guar gum is not less than 2000 cP.

12. A composition as claimed in claim 6, wherein the nominal viscosity at 25° C. of a 1% w/w aqueous solution of hydroxypropylcellulose is not less than 1500cP; the nominal viscosity at 25° C. of a 1% w/w aqueous solution of hydroxyethylcellulose is not less than 1500 cP; the nominal viscosity at 25° C. of a 1% w/w aqueous solution of sodium carboxymethylcellulose is not less than 1500 cP; and the nominal viscosity at 25° C. of a 1% w/w aqueous solution of xanthan gum is not less than 1200 cP.

13. A composition as claimed in claim 7, wherein disintegrants are selected from starch, sodium starch glycollate, crosscarmellose sodium, crospovidone, pregelatinized starch, microcrystalline cellulose and hydroxypropylcellulose.

14. A composition as claimed in claim 4, wherein the pH independent prolonged in-vitro release of biguanide from the type I first layer at the end of 1, 4 and 8 hours lies in the range of 25-45% w/w, 50-80% w/w and not less than 75% w/w respectively and the in-vitro release of the one or more pharmaceutically acceptable ingredients, or pharmaceutical acceptable salts thereof from the immediate release layer at the end of 30 minutes is not less than 80% w/w.

15. A composition as claimed in claim 4, wherein the first layer comprises Metformin hydrochloride in the range of 500-2000 mg and the second layer comprises Pioglitazone hydrochloride equivalent to Pioglitazone in the range of 15-60 mg.

16. A composition as claimed in claim 4, wherein the prolonged release layer comprises Metformin hydrochloride in an amount of at least 48% w/w of that layer and the immediate release layer comprises Pioglitazone hydrochloride in an amount from 5% to 30% w/w of that layer.

17. A pharmaceutical composition as claimed in claim 4, wherein the composition comprises at least 48% w/w of Metformin hydrochloride of particle size less than 100 microns and at least one polymer selected from alkylcellulose, hydroxyalkylcellulose and carboxyalkylcellulose or pharmaceutical acceptable salts thereof, (meth)acrylic acid copolymers, xanthan gum, guar gum, alginates or pharmaceutically acceptable salts thereof, the polymer(s) being present in an amount of at least 35% by weight of Metformin hydrochloride in the composition.

18. A process as claimed in claim 1, wherein step a) comprises:
    i. blending Metformin hydrochloride with at least one non-biodegradable inert polymer selected from alkylcellulose, hydroxyalkylcellulose and carboxyalkylcellulose or pharmaceutical acceptable salts thereof, (meth)acrylic acid copolymers, xanthan gum, guar gum, alginates or pharmaceutically acceptable salts thereof to obtain Metformin hydrochloride-polymer blend, the polymer(s) being present in an amount of at least 35% by weight of Metformin hydrochloride in the dosage form and Metformin hydrochloride being present in an amount of at least 48% by weight of dosage form;
    ii. wet granulating the Metformin hydrochloride-polymer blend using water or hydroalcoholic solution optionally containing binder and plasticizer; and
    iii. drying, sizing, lubricating and compressing the granulated mass.

19. A method of treating diabetes in a mammal in need thereof, comprising administering a bi-layer tablet dosage form to the mammal once a day, wherein the tablet dosage form comprises,
    a) a first layer comprising granules of at least one non-biodegradable inert polymer and a biguanide, or a pharmaceutically acceptable salt thereof, of particle size less than 100 microns for pH independent prolonged in-vitro release of the biguanide or pharmaceutical acceptable salts thereof, wherein the non-biodegradable inert polymer is present in an amount of at least 35% by weight of biguanide in the dosage form; and
    b) a second layer for immediate release comprising (i) one or more active pharmaceutical ingredients, or pharmaceutical acceptable salts thereof, selected from thiazolidinediones, sulfonyl ureas, alpha-glucosidase inhibitors, aldose reductase inhibitors, statins, squalene synthesis inhibitors, fibrates, angiotensin converting enzymes inhibitor inhibitors, and LDL catabolism enhancers and (ii) a non-biodegradable inert polymer;
    wherein the content of non-biodegradable inert polymer in the second layer is not more than 1.2% by weight of the second layer, and the dosage form provides monophasic prolonged release of the biguanide.

20. A method as claimed in claim 19, wherein the first layer comprises Metformin hydrochloride and the second layer comprises Pioglitazone, Rosiglitazone, Troglitazone, or a pharmaceutical acceptable salt thereof.

* * * * *